United States Patent [19]

Kashima et al.

[11] Patent Number: 4,922,010

[45] Date of Patent: May 1, 1990

[54] PROCESSES FOR PREPARING 2-SUBSTITUTED PROPIONIC ACID AND DERIVATIVES THEREOF

[75] Inventors: Mikito Kashima, Ichihara; Hideo Ishikawa, Minoo; Kouichi Kashiwagi; Yumiki Noda, both of Ichihara, all of Japan

[73] Assignee: Ube Industries, Ltd., Yamaguchi, Japan

[21] Appl. No.: 282,024

[22] Filed: Dec. 7, 1988

[30] Foreign Application Priority Data

Dec. 18, 1987 [JP] Japan .................................. 62-318678
Dec. 18, 1987 [JP] Japan .................................. 62-318679
Sep. 27, 1988 [JP] Japan .................................. 63-239839

[51] Int. Cl.$^5$ ...................... C07C 59/48; C07C 59/64
[52] U.S. Cl. ..................................... 562/470; 562/466
[58] Field of Search ........................................ 562/470

[56] References Cited

FOREIGN PATENT DOCUMENTS 3002449 11/1978 Japan .

*Primary Examiner*—Paul J. Killos
*Attorney, Agent, or Firm*—Frishauf, Holtz, Goodman & Woodward

[57] ABSTRACT

There are disclosed a process for preparing 2-hydroxy-2-(6-methoxy-2-naphthyl)propionic acid or 2-hydroxy-2-(4-substituted phenyl)propionic acid derivative which comprises reacting 2-methoxynaphthalene or substituted benzene derivatives with pyruvic acid in the presence of a Lewis acid and then, if necessary, hydrolyzing the obtained product, and a process for preparing 2-(6-methoxy-2-naphthyl)propionic acid or 2-(4-substituted phenyl)propionic acid derivative which comprises reducing 2-hydroxy-2-(6-methoxy-2-naphthyl)propionic acid or 2-hydroxy-2-(4-substituted phenyl)propionic acid derivative in a lower aliphatic acid in the presence of an inorganic acid under hydrogen atmosphere by using a metal catalyst.

12 Claims, No Drawings

PROCESSES FOR PREPARING 2-SUBSTITUTED PROPIONIC ACID AND DERIVATIVES THEREOF

BACKGROUND OF THE INVENTION

This invention relates to processes for preparing 2-(6-methoxy-2-naphthyl)propionic acid which is an available pharmaceutical having antiphlogistic, analgesic and antipyretic actions, for preparing 2-hydroxy-2-(6-methoxy-2-naphthyl)propionic acid which is extremely useful as a precursor for preparing the above compound, and for preparing 2-hydroxy-2-(4-substituted phenyl)propionic acid which is extremely useful as a precursor for preparing 2-(4-substituted phenyl)propionic acid which is usable as a pharmaceutical having antiphlogistic, analgesic and antipyretic actions.

As the method for preparing 2-(6-methoxy-2-naphthyl)propionic acid, there has hitherto been known the methods as disclosed in Japanese Patent Publications No. 702/1973 and No. 31981/1974.

In Japanese Patent Publication No. 702/1973, there is disclosed the method in which 2-(6-methoxy-2-naphthyl)propionic acid is prepared from 2-methoxynaphthalene via 7 steps by using sodium hydride and methyl iodide.

Also, in Japanese Patent Publication No. 31981/1974, there is disclosed the method in which 2-(6-methoxy-2-naphthyl)propionic acid is prepared from 2-naphthol via 7 steps by using dimethyloxosulfoniummethylide.

These methods are many in preparation steps and require complicated operations, and yet these methods require a substarting material which is highly dangerous or expensive so that they include many problems.

Also, as the method for preparing 2-(6-methoxy-2-naphthyl)propionic acid from 2-hydroxy-2-(6-methoxy-2-naphthyl)propionic acid or ester derivatives thereof, there are methods as disclosed in Japanese Provisional Patent Publications No. 4136/1976, No. 105144/1977 and No. 16437/1980. In the methods of these publications, they involve the problem that an expensive material such as hydroiodic acid is required. In Japanese Provisional Patent Publication No. 4136/1976, there is disclosed the method in which 2-(6-methoxy-2-naphthyl)acrylic acid is synthesized from 2-hydroxy-2-(6-methoxy-2-naphthyl)propionic acid by the dehydration reaction and then reducing the compound or the method in which 2-halogeno-2-(6-methoxy-2-naphthyl)propionic acid is synthesized from 2-hydroxy-2-(6-methoxy-2-naphthyl)propionic acid and then reducing the compound, but these methods have the problem that steps become likely longer. Also, the method disclosed in Japanese Provisional Patent Publication No. 16437/1977 requires to use expensive quaternary ammonium salts or bromoform so that it involves the problem.

Also, the conventional catalytic reduction using no acid catalyst requires a long reaction time and the reduction using a metal requires a large amount of metal. Other methods are also unsuitable methods from the industrial view point.

As the other literature of the preparative method of 2-(6-methoxy-2-naphthyl)propionic acid, there may be mentioned EP-A-0 184 573, EP-A-0 189 120 and DE-A-26 13 817 (German Offenlegungsschrift).

In the methods disclosed in EP-A-0 184 573 and DE-A-26 13 817, many producing steps and complicated operations are necessary for obtaining 2-hydroxy-2-(6-methoxy-2-naphthyl)propionic acid. In the method disclosed in EP-A-0 189 120, electrolytic reaction should be carried out so that there involves many problems.

While there is no literature describing a 2-hydroxy-2-(4-substituted)propionic acid derivatives which are one of the compounds to be prepared by the method of the present invention, if the methods disclosed in the above literatures are applied thereto, there involve the same problems as mentioned above and thus, establishment of an excellent industrial preparative method has been desired.

SUMMARY OF THE INVENTION

An object of the present invention is to provide a process for preparing 2-substituted propionic acid derivatives with one step and easily.

The present inventors have investigated earnestly in view of the above situation, and as the results, they have found industrial processes for preparing 2-hydroxy-2-(6-methoxy-2-naphthyl)propionic acid from 2-hydroxy-2-(6-methoxy-2-naphthyl)propionic acid, 2-hydroxy-2-(4-substituted phenyl)propionic acid and 2-(4-substituted phenyl)propionic acid each with one step and easily to accomplish the present invention.

That is, the present invention provides a process for preparing 2-hydroxy-2-(6-methoxy-2-naphthyl)propionic acid or 2-hydroxy-2-(4-substituted phenyl)propionic acid derivatives represented by the following formula (I):

$$H_3C-CR-COOH \quad (I)$$
$$|$$
$$OH$$

wherein R represents

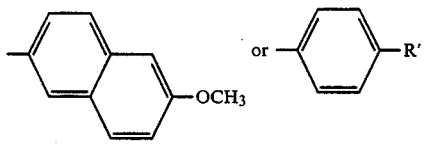

where R' represents a straight or branched alkyl group having 1 to 5 carbon atoms, a phenoxy group or a phenoxy group substituted by a halogen atom or a straight or branched alkyl group having 1 to 5 carbon atoms,
which comprises reacting 2-methoxynaphthalene or substituted benzene derivatives represented by the formula (II):

wherein R' has the same meaning as defined above, with pyruvic acid or pyruvic acid ester derivatives in the presence of a Lewis acid and then hydrolyzing the obtained product when the pyruvic acid ester derivatives are used.

The present invention also provides (3) a process for preparing 2-(6-methoxy-2-naphthyl)propionic acid or 2-(4-substituted phenyl)propionic acid derivatives represented by the formula (III):

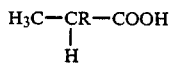

(III)

wherein R has the same meanings as defined above, which comprises reducing the compound of the formula (I) in a lower aliphatic acid in the presence of an inorganic acid under hydrogen atmosphere by using a metal catalyst.

DESCRIPTION OF THE PREFERRED EMBODIMENTS

As the pyruvic acid ester derivatives in the process of preparing the compound of the formula (I), there may be mentioned pyruvic acid lower alkylester derivatives, and more specifically methyl pyruvate, ethyl pyruvate, propyl pyruvate, 1-methylethyl pyruvate, butyl pyruvate, 1-methylpropyl pyruvate, 2-methylpropyl pyruvate, pentyl pyruvate, 3-methylbutyl pyruvate, etc.

An amount of pyruvic acid or pyruvic acid ester derivatives to be used is generally 0.3 to 4 times moles, preferably 0.5 to 2.5 times moles based on 2-methoxynaphthalene or substituted benzenes.

The substituted benzene derivatives to be used in the process for preparing 2-hydroxy-2-(4-substituted phenyl)propionic acid of the present invention may include the diphenyl ether derivative represented by the following formula (IV):

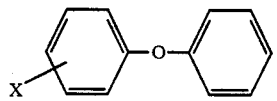

(IV)

wherein X represents a halogen atom or a straight or branched alkyl group having 1 to 5 carbon atoms.

Concrete examples thereof may include diphenyl ether, 4-chlorodiphenyl ether, 4-bromodiphenyl ether, 4-iododiphenyl ether, 4-methyldiphenyl ether, 4-ethyldiphenyl ether, 4-isopropyldiphenyl ether, etc.

Further, the substituted benzene derivatives of the present invention may include the benzene derivatives represented by the following formula (V):

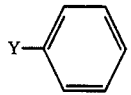

(V)

wherein Y represents a straight or branched alkyl group having 1 to 5 carbon atoms.

Concrete examples thereof may include toluene, ethylbenzene, isopropylbenzene, t-butylbenzene, etc.

Concrete example of the 2-hydroxy-2-(4-substituted phenyl)propionic acid or derivatives thereof prepared by the above method may include 2-hydroxy-2-(4-isobutylphenyl)propionic acid, 2-hydroxy-2-(4-phenoxyphenyl)propionic acid, 2-hydroxy-2-(4-(4'-chlorophenoxy)phenyl)propionic acid, 2-hydroxy-2-(4-(4'-methylphenoxy)phenyl)propionic acid, 2-hydroxy-2-(4-methylphenyl)propionic acid, 2-hydroxy-2-(4-isopropylphenyl)propionic acid and the like.

As the Lewis acid, an inorganic acid is preferably used. Concrete examples thereof may include anhydrides of aluminum chloride, aluminum bromide, titanium tetrachloride, boron trifluoride, zinc chloride, stannic chloride, ferric chloride, etc.; and sulfuric acid, hydrogen chloride, and the like. Among them, anhydrous aluminum chloride is particularly preferably used.

An amount of the Lewis acid to be used is generally 0.1 to 7 times moles, preferably 0.5 to 3 times moles based on pyruvic acid or ester derivatives thereof.

As the solvent for the reaction, preferably used are methylene chloride, dichloroethane, tetrachloroethane, chlorobenzene, o-dichlorobenzene, carbon disulfide, benzene, toluene, nitrobenzene, nitroethane, acetic acid and mixed solvent of the above. Among them, methylene chloride is particularly preferably used.

A reaction pressure is generally preferably normal pressure or a pressurized condition. Under the pressurized condition, a reaction time can be shortened while under the normal pressure, operation of a device is easy.

A reaction temperature is generally −60° to 60° C., preferably −40° to 30° C. If the temperature is excessively low, yield of the product to be obtained lowers as well as the reaction time becomes longer. To the contrary, if the temperature becomes excessively high, yield of the product to be obtained becomes low due to formation of a by-product(s).

A reaction time in the presence of the Lewis acid including dropwise addition and stirring is generally 0.1 to 30 hours, preferably 0.4 to 10 hours. If the reaction time is too short, yield of the product to be obtained lowers, but if it is too long, by-products increase.

After completion of the reaction, the solvent is removed. Then, by using the residue as it were when the pyruvic acid is used or the residue after carrying out hydrolysis with an alkaline solution when the pyruvic acid ester derivative is used, recrystallization by making it acidic, and isolation are carried out. Hydrolysis of the ester is generally carried out with sodium hydroxide or potassium hydroxide. An amount of sodium hydroxide or potassium hydroxide to be used is 1 to 10 times moles, preferably 1.2 to 5 times moles per mole of the starting pyruvic acid ester derivative.

The lower aliphatic acid to be used in the process for preparing the compound of the formula (III) is used as a solvent, and concrete examples thereof may include formic acid, acetic acid, propionic acid, n-butyric acid, iso-butyric acid, n-valeric acid, iso-valeric acid, sec-valeric acid, etc. Among them, acetic acid is particularly preferably used. An amount of the lower aliphatic acid to be used is generally 0.5 to 50 times weigh amounts, preferably 2 to 20 times weight amounts based on the compound of the formula (I).

As a concentration in solution, an amount of the compound of the formula (I) is 2 to 65% (weight), preferably 10 to 35% (weight) based on the lower aliphatic acid. If the concentration of the above is too low, the reaction rate becomes slow whereby yield of the compound of the formula (III) becomes low. Also, if the concentration is too dense, a uniform solution cannot be obtained whereby yield of the compound of the formula (III).

Concrete examples of the organic acid may include sulfuric acid, hydrochloric acid, phosphoric acid and boric acid. Among them, sulfuric acid is particularly preferably used. An amount of the inorganic acid to be used is 0.01 to 1 time (weight ratio), preferably 0.02 to 0.3 times (weight) based on the compound of the formula (I).

The metal catalyst to be used in the present invention may include catalysts of palladium series, rhodium series, ruthenium series, etc. Among them, from a view point of easily handling, palladium metal-carbon hydrogenolysis catalyst is suitable. An amount of the metal catalyst to be used is generally, in terms of metal weight, 0.00001 to 0.1 time (weight ratio), preferably 0.0001 to 0.01 time (weight ratio) based on the compound of the formula (I).

Further, an amount of the inorganic acid to be used is 0.0001 to 1.0 time (weight ratio), preferably 0.002 to 0.2 time (weight ratio) based on the amount of the metal catalyst.

A reaction pressure is preferably normal pressure or a pressurized condition. Under the pressurized condition, a reaction time can be shortened while under the normal pressure, operation of a device is easy. More specifically, the reaction is carried out under a pressure of normal pressure to 100 Kg/cm$^2$ G, more preferably 5 to 50 Kg/cm$^2$ G.

A reaction temperature is generally normal temperature to 150° C., preferably 70° to 130° C. If the temperature is too high, the compound of the formula (I) is decarboxylated whereby yield of the product to be obtained lowers. To the contrary, if the temperature becomes too low, yield of the product becomes low due to decrease of solubility of the compound of the formula (I) to a solvent and due to lowering in the reaction rate.

A reaction time is generally 2 to 30 hours, preferably 3 to 20 hours. If the reaction time is too short, the reaction is insufficient whereby yield of the product lowers. On the other hand, if the reaction time is too long, a ratio of conversion per unit time lowers so that it is of no use.

EXAMPLES

In the following, Examples of the present invention will be shown. In Examples 1 to 7, yields are shown by the value based on 2-methoxynaphthalene.

EXAMPLE 1

In 15 ml of methylene chloride were placed 1.58 g (0.01 mole) of 2-methoxynaphthalene and 1.50 g (0.011 mole) of anhydrous aluminum chloride, and a solution of 0.91 g (0.01 mole) of pyruvic acid dissolved in 5 ml of methylene chloride was added dropwise to the mixture at 5° to 7° C. over 20 minutes. After the reaction at the temperature for 5 hours (a time from initiating dropwise addition), the reaction mixture was poured into ice-cold water, added 6 ml of conc. hydrochloric acid and extracted twice with methylene chloride.

After washing with water, the extract was extracted with a 5% sodium hydrogen carbonate aqueous solution and washed with methylene chloride. A diluted hydrochloric acid was added to the aqueous layer to make it acidic and precipitated crystals were subjected to suction filtration to give 0.24 g of 2-hydroxy-2-(6-methoxy-2-naphthyl)propionic acid. Yield: 10%.

m.p.: 154° to 156° C.

IR (cm$^{-1}$): 3420, 3300 to 2500, 1710.

NMR (CD$_3$COCD$_3$): 1.84 (3H), 3.91 (3H), 7.15 (1H), 7.28 (1H), 7.6 to 7.9 (3H), 8.06 (1H).

EXAMPLE 2

In 150 ml of methylene chloride were placed 47.46 g (0.300 mole) of 2-methoxynaphthalene and 58.76 g (0.441 mole) of anhydrous aluminum chloride, and 36.76 g (0.360 mole) of methyl pyruvate was added dropwise to the mixture at 1° to 5° C. over 1 hour and 55 minutes while stirring.

Further, after stirring for 5 minutes, the reaction mixture was poured into ice-cold water and the mixture was stirred by adding 100 ml of conc. hydrochloric acid. The methylene chloride layer was separated and washed with water. After drying over anhydrous magnesium sulfate, methylene chloride was removed. To the residue were added a sodium hydroxide aqueous solution prepared from 30.30 g of sodium hydroxide and 200 ml of water, and 150 ml of toluene, and then 70 ml of ethanol and 100 ml of water were further added thereto. The mixture was stirred at 80° C. for 32 hours. During the mixture being hot, the aqueous layer was added dropwise while stirring in hydrochloric acid (prepared from 70 ml of conc. hydrochloric acid and 200 ml of water) cooled with ice-cold water. Precipitated crystals were subjected to suction filtration, washed with water and then washed with 100 ml of 50% toluene-hexane to give 55.52 g of 2-hydroxy-2-(6-methoxy-2-naphthyl)propionic acid. Yield: 75%.

From NMR spectrum and IR spectrum, the structure thereof was confirmed.

m.p.: 154° to 156° C.

IR (cm$^{-1}$): 3420, 3300 to 2500, 1710.

NMR (CD$_3$COCD$_3$): 1.84 (3H), 3.91 (3H), 7.15 (1H), 7.28 (1H), 7.6 to 7.9 (3H), 8.06 (1H).

EXAMPLE 3

In 30 ml of methylene chloride were placed 9.49 g of 2-methoxynaphthalene and 16.62 g of powdered anhydrous aluminum chloride, and 6.74 g of methyl pyruvate was added dropwise to the mixture at −15° to −10° C. over 30 minutes while stirring. After stirring the mixture at the temperature for 30 minutes, it was poured into ice-cold water. To the mixture was added 40 ml of conc. hydrochloric acid and the mixture was stirred. Methylene chloride separated from the aqueous solution was removed and 13.77 g of the residue thus obtained was dissolved by adding 40 ml of toluene. A potassium hydroxide aqueous solution was added to the solution, and the mixture was stirred at 70° C. for one hour.

The aqueous layer was separated, and hydrochloric acid prepared from 12.5 ml of conc. hydrochloric acid and 40 ml of water was added dropwise thereto during the aqueous layer being hot while stirring. After allowed to stand for cooling, precipitated crystals were subjected to suction filtration and washed with water. These crystals were dried under reduced pressure to give 10.30 g of 2-hydroxy-2-(6-methoxy-2-naphthyl)propionic acid. Yield: 70%.

EXAMPLE 4

In 50 ml of methylene chloride were placed 14.23 g of 2-methoxynaphthalene and 8.80 g of anhydrous aluminum chloride, and a solution containing 6.13 g of methyl pyruvate dissolved in 20 ml of methylene chloride was added dropwise to the mixture at 2.5° to 4° C. over 55 minutes while stirring. After stirring the mixture for further 20 minutes, it was poured into ice-cold water and the methylene chloride layer was separated and washed with water. It was dried over anhydrous magnesium sulfate and methylene chloride was removed. The residue was dissolved in 55 ml of ethanol, and then, by adding a solution containing 9.90 g of potassium hydroxide dissolved in 65 ml of ethanol, the mixture was stirred at room temperature for 2 hours. After ethanol was removed under reduced pressure, by adding water and toluene, the mixture was extracted with water. The aqueous layer was added dropwise into a diluted hydrochloric acid prepared from 13.5 ml of conc. hydrochloric acid and 50 ml of water while stirring. The precipitated crystals were subjected to suction filtration and washed with 40 ml of 50% hexane-benzene. After drying under reduced pressure, 6.59 g of 2-hydroxy-2-(6-methoxy-2-naphthyl)propionic acid. Yield: 30%.

EXAMPLE 5

In 25 ml of chlorobenzene were placed 3.16 g of 2-methoxynaphthalene and 3.20 g of anhydrous aluminum chloride. By dissolving 2.04 g of methyl pyruvate in 10 ml of chlorobenzene, the solution was added dropwise to the above mixture at 8° to 10° C. over 27 minutes while stirring. After stirring the mixture for further 15 minutes, ice-cold water was added thereto and the chlorobenzene layer was separated. After washing with water, the chlorobenzene layer was dried over anhydrous magnesium sulfate. By removing chlorobenzene under reduced pressure, the residue was dissolved in 8 ml of ethanol. A solution of 2.64 g of potassium hydroxide dissolved in 10 ml of ethanol was added thereto, and the mixture was stirred at room temperature for 4.5 hours. By removing ethanol, ether and water were added thereto and the mixture was extracted with water.

The aqueous layer was added dropwise in a diluted hydrochloric acid prepared from 4.2 ml of conc. hydrochloric acid and 30 ml of water while stirring. The precipitated crystals were subjected to suction filtration and then washed with water. Subsequently, these crystals were washed with hexane and subjected to drying under reduced pressure to give 1.76 g of 2-hydroxy-2-(6-methoxy-2-naphthyl)propionic acid. Yield: 36%.

EXAMPLE 6

In 20 ml of o-dichlorobenzene were placed 1.58 g of 2-methoxynaphthalene and 2.93 g of anhydrous aluminum chloride. By dissolving 2.04 g of methyl pyruvate in 5 ml of o-dichlorobenzene, the solution was added dropwise to the above mixture at 7° to 11° C. over 13 minutes while stirring. After stirring the mixture for further 30 minutes, ice-cold water was added thereto and the o-dichlorobenzene layer was separated. After washing with water, the o-dichlorobenzene layer was dried over anhydrous magnesium sulfate. By removing o-dichlorobenzene under reduced pressure, the residue was subjected to the same procedure as in Example 3 to give 0.80 g of 2-hydroxy-2-(6-methoxy-2-naphthyl)propionic acid. Yield: 33%.

EXAMPLE 7

In a 3 liters of three-necked flask were placed 158.20 g (1.0 mole) of 2-methoxynaphthalene, 192.0 g (1.44 moles) of aluminum chloride and 500 ml of methylene chloride at room temperature while the reaction system being made to a nitrogen atmosphere. Cooling the apparatus with ice-salt bath, and the temperature of the mixture was made to 3° to 7° C. To the mixture was added dropwise 126.20 g (1.20 moles) of methyl pyruvate over 2 hours and 40 minutes. After completion of the dropwise addition, the mixture was stirred at the same temperature for 10 minutes. Subsequently, the reaction mixture was poured into 600 ml of a 15% HCl at 0° to 5° C. to stop the reaction. The methylene chloride layer was separated therefrom, and washed twice with 400 ml of water. This was condensed and then 400 ml of toluene, 150 ml of ethanol and 700 ml of a 13% sodium hydroxide aqueous solution were added to the residue, and the mixture was stirred at 70° C. for 2 hours. After cooled to the room temperature, the tolene layer was separated.

The aqueous layer was added to 1500 ml of a 9% HCl and the mixture was stirred for 30 minutes. Precipitated crystals were collected by filtration, dried under reduced pressure of 5 mmHg at 50° C. for 15 hours to give 140.37 g of crude 2-hydroxy-2-(6-methoxy-2-naphthyl)propionic acid. Yield of crude: 57%. This crude crystals were recrystallized from ethanol-water to give 121.8 g of a purified product. Yield: 49%.

EXAMPLE 8

In 10 ml of glacial acetic acid were placed 2.00 g of 2-hydroxy-2-(6-methoxy-2-naphthyl)propionic acid and 0.07 g of a 2% (weight) palladium-carbon, and then 0.5 ml of a 10% sulfuric acid aqueous solution to the mixture. After reduced the system, an atmosphere was replaced twice with a nitrogen gas, and then replaced twice with a pure hydrogen gas to effect the reaction at a normal pressure under a hydrogen atmosphere. After the reaction was carried out at 100° C. for 15.5 hours and the mixture was allowed to stand for cooling, the system was reduced and replaced twice with a nitrogen gas to make it a nitrogen atmosphere. Acetic acid was removed under reduced pressure and methylene chloride was added to the residue, and then the catalyst was removed by filtration. The filtrate was washed twice with water and dried over anhydrous magnesium sulfate.

Solids obtained by removing methylene chloride was recrystallized from toluene to give 1.80 g of 2-(6-methoxy-2-naphthyl)propionic acid. Yield to 2-hydroxy-2-(6-methoxy-2-naphthyl)propionic acid is 96%. m.p. 149.5° to 151.5° C.

From NMR spectrum and IR spectrum, the structure thereof was confirmed.

NMR (CDCl$_3$): 1.57 (3H), 3.90 (3H), 7.10 (1H), 7.12 (1H), 7.40 (1H), 7.6 to 7.7 (3H).

IR (cm$^{-1}$): 3500 to 2500, 1700.

EXAMPLE 9

In a 300 ml of an autoclave were charged 9.85 g (40 mmole) of crude 2-hydroxy-2-(6-methoxy-2-naphthyl)propionic acid, 60 ml of acetic acid, 2.5 ml of a 10% sulfuric acid and 0.34 g of a 2% palladium-carbon, and the atmosphere thereof was replaced three times with 80 kg/cm$^2$ of a hydrogen gas. A hydrogen pressure was set to 20 kg/cm$^2$ and the reaction was carried out at 100° C. for 6 hours.

After allowed to stand for cooling, the palladium-carbon was removed by filtration, 200 ml of chloroform and 150 ml of water were added to the filtrate and the chloroform layer was separated therefrom. The chloroform layer was washed twice with 150 ml of water and dried over anhydrous magensium sulfate. Chloroform was removed therefrom to give 7.35 g (crude yield: 80%) of 2-(6-methoxy-2-naphthyl)propionic acid.

EXAMPLE 10

In a 100 ml of an autoclave were charged 1.97 g (8 mmole) of 2-hydroxy-2-(6-methoxy-2-naphthyl)propionic acid which had been purified by recrystallization, 10 ml of acetic acid, 0.5 ml of a 10% sulfuric acid and 0.07 g of a 2% palladium-carbon, and the atmosphere thereof was replaced three times with 80 kg/cm² of a hydrogen gas. Thereafter, a hydrogen pressure of the reaction system was set to 20 kg/cm² and the reaction was carried out at 100° C. for 6 hours.

After allowed to stand for cooling, the palladium-carbon was removed by filtration, 100 ml of chloroform and 70 ml of water were added to the filtrate and the chloroform layer was separated therefrom. The chloroform layer was washed twice with 70 ml of water and dried over anhydrous magensium sulfate. Chloroform was removed therefrom to give 1.76 g (yield: 96%) of 2-(6-methoxy-2-naphthyl)propionic acid.

EXAMPLE 11

In a 50 ml of a reactor equipped with a stirrer, a cooling tube and a dropping funnel were charged 2.63 g (19.6 mmole) of isobutylbenzene, 3.20 g (24 mmole) of anhydrous aluminum chloride and 12 ml of methylene chloride under a nitrogen atmosphere, and the mixture was stirred under ice-cooling. To the mixture was added dropwise through the dropping funnel 2.50 g (24.5 mmole) of methyl pyruvate so as to not exceed the liquid temperature of 10° C. After completion of the dropwise addition, the reaction was further continued for further 30 minutes at the same temperature while stirring.

After completion of the reaction, 15 ml of a 5% hydrochloric acid was gradually added to the reaction mixture to decompose aluminum chloride. To the decomposed solution, 10 ml of methylene chloride was added for extraction and the aqueous layer and the methylene chloride layer were separated. The separated methylene chloride layer was washed with 10 ml of a 5% hydrochloric acid and with 10 ml of a 5% sodium bicarbonate aqueous solution.

The methylene chloride layer was condensed by vacuum distillation. To the condensed residue were added 15 ml of a 13% sodium hydroxide aqueous solution, 10 ml of toluene and 4 ml of ethanol, and reaction was carried out at 80° C. for 3 hours. After cooled the reaction mixture, the aqueous layer and the oily layer were separated, and the aqueous layer was made acidic by adding a 9% hydrochloric acid. To this mixture was added 30 ml of isopropyl ether, and extraction and separation of liquids were carried out. The isopropyl ether layer was condensed, and the condensed residue was recrystallized from a mixed solvent of ethanol and hexane to give 1.22 g (5.49 mmole) of the aimed 2-hydroxy-2-(4-isobutylphenyl)propionic acid. Yield based on isobutylbenzene was 28%.

EXAMPLE 12

In a reactor used in Example 11, 1.70 g (10.0 mmole) of diphenyl ether, 1.73 g (13 mmole) of anhydrous aluminum chloride and 5 ml of methylene chloride were charged therein under a nitrogen atmosphere, and the mixture was stirred under ice-cooling.

To the mixture was added dropwise through the dropping funnel 1.23 g (12.0 mmole) of methyl pyruvate so as to not exceed the liquid temperature of 10° C. After completion of the dropwise addition, the reaction was further continued for further 30 minutes at the same temperature while stirring.

After completion of the reaction, 10 ml of a 5% hydrochloric acid was gradually added to the reaction mixture to decompose aluminum chloride. To the decomposed solution, 10 ml of methylene chloride was added for extraction and the aqueous layer and the methylene chloride layer were separated. The separated methylene chloride layer was washed with 5 ml of a 5% hydrochloric acid and with 5 ml of a 5% sodium bicarbonate aqueous solution. The methylene chloride layer was dried over anhydrous magnesium sulfate and after the magnesium sulfate was removed by filtration, it was condensed. The condensed residue was purified through column chromatography (silica gel; eluent: toluene, toluene:methylene chloride=1:1) to give 1.20 g (4.40 mmole) of the aimed methyl 2-hydroxy-2-(4-phenoxyphenyl)propionate. Yield was 44%.

EXAMPLE 13

To 1.18 g of 2-hydroxy-2-(4-isobutylphenyl)propionic acid were added 10 ml of acetic acid, 0.5 ml of a 10% sulfuric acid and 0.08 g of a 2% palladium-carbon, and hydrogen was supplied in the reaction system by using a hydrogen balloon. After reaction was carried out at 100° C. for 15 hours while stirring, the hydrogen balloon was removed and the atmosphere was replaced with nitrogen. Subsequently, acetic acid was removed under the conditions of 10 mmHg at 60° C.

To the residue was added 20 ml of isopropyl ether and the palladium-carbon was removed by filtration, and the isopropyl ether layer of the filtrate was washed three times with 10 ml of water. The isopropyl layer was then further dehydrated with anhydrous magnesium sulfate. After removed magnesium sulfate by filtration, isopropyl ether was removed at 80° C. to give 0.91 g of the aimed 2-(4-isobutylphenyl)propionic acid. Yield was 83%.

According to the present invention, 2-(6-methoxy-2-naphthyl)propionic acid or 2-(4-substituted phenyl)propionic acid can be produced from 2-hydroxy-2-(6-methoxy-2-naphthyl)propionic acid or 2-hydroxy-2-(4-substituted phenyl)propionic acid, respectively, with one step reaction easily and cheaply.

Also, according to the present invention, an industrial method which is capable of producing 2-hydroxy-2-(6-methoxy-2-naphthyl)propionic acid or 2-hydroxy-2-(4-substituted phenyl)propionic acid with one step in producing step and easy reaction procedure.

We claim:

1. A process for preparing 2-hydroxy-2-(6-methoxy-2-naphthyl)propionic acid or 2-hydroxy-2-(4-substituted phenyl)propionic acid derivatives represented by the following formula (I):

$$H_3C-CR-COOH \atop OH \qquad (I)$$

wherein R represents

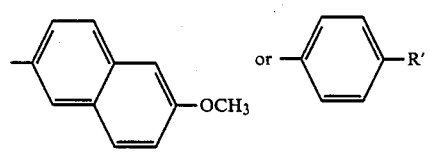

where R' represents a phenoxy group or a phenoxy group substituted by a halogen atom or a straight or branched alkyl group having 1 to 5 carbon atoms, which comprises reacting 2-methoxynaphthalene or a substituted benzene derivatives represented by the formula (II):

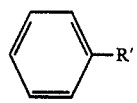
(II)

wherein R' has the same meaning as defined above, with pyruvic acid or pyruvic acid ester derivatives in the presence of a Lewis acid and then hydrolyzing the obtained product when the pyruvic acid ester derivatives are used.

2. A process according to claim 1, wherein the substituted benzene derivatives are diphenyl ether derivative represented by the following formula (IV):

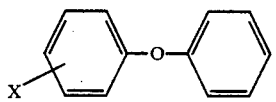
(IV)

wherein X represents a halogen atom or a straight or branched alkyl group having 1 to 5 carbon atoms.

3. A process according to claim 2, wherein the substituted benzene derivatives are the diphenyl ether derivative represented by the following formula (IV):

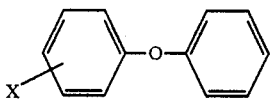
(IV)

wherein X is as defined in claim 2.

4. A process according to claim 2, wherein said benzene derivative is selected from the group consisting of diphenyl ether, 4-chlorodiphenyl ether, 4-bromodiphenyl ether, 4-iododiphenyl ether, 4-methyldiphenyl ether, 4-ethyldiphenyl ether and 4-isopropyldiphenyl ether.

5. A process for preparing 2-(6-methoxy-2-naphthyl)-propionic acid or 2-(4-substituted phenyl)propionic acid derivatives represented by the formula (III):

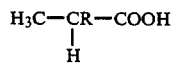
(III)

wherein R represents

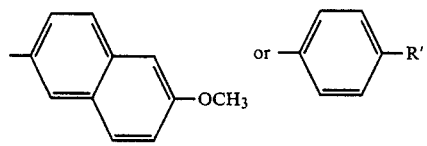

where R' represents, a phenoxy group or a phenoxy group substituted by a halogen atom or a straight or branched alkyl group having 1 to 5 carbon atoms, which comprises reducing the compound of the formula (I):

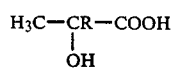
(I)

wherein R has the same meaning as defined above, in a lower aliphatic acid in the presence of an inorganic acid under hydrogen atmosphere by using a metal catalyst.

6. A process according to claim 5, wherein the reaction is carried out under a pressurized condition.

7. The process of claim 5, further comprising the step of preparing the compound of formula (I) by reacting 2-methoxynaphthalene or a substituted benzene derivative represented by the formula (II):

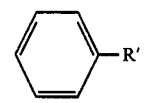
(II)

wherein R' has the same meaning as defined in claim 6, with a pyruvic acid ester derivative in the presence of a Lewis acid; and thereafter, hydrolyzing the obtained product.

8. A process according to claim 7, wherein the substituted benzene derivatives are diphenyl ether derivatives represented by the following formula (IV):

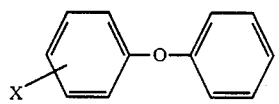
(IV)

wherein X represents a halogen atom or a straight or branched alkyl group having 1 to 5 carbon atoms.

9. A process according to claim 8, wherein the substituted benzene derivatives are the diphenyl ether derivatives represented by the following formula (IV):

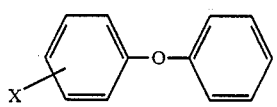
(IV)

wherein X is as defined in claim 8.

10. A process according to claim 8, wherein said benzene derivative is selected from the group consisting of diphenyl ether, 4-chlorodiphenyl ether, 4-bromodiphenyl ether, 4-iododiphenyl ether, 4-methyldiphenyl ether, 4-ethyldiphenyl ether and 4-isopropyldiphenyl ether.

11. A process according to claim 5, further comprising the step of preparing the compound of formula (I) by reacting a diphenyl ether derivative represented by the following formula (IV):

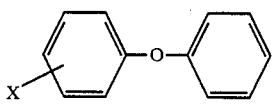
(IV)

wherein X represents a halogen atom or a straight or branched alkyl group having 1 to 5 carbon atoms; with a pyruvic acid ester derivative in the presence of a Lewis Acid; and thereafter hydrolyzing the obtained product.

12. A process according to claim 11, wherein said benzene derivative is selected from the group consisting of diphenyl ether, 4-chlorodiphenyl ether, 4-bromodiphenyl ether, 4-iododiphenyl ether, 4-methyldiphenyl ether, 4-ethyldiphenyl ether, 4-isopropyldiphenyl ether.

* * * * *